United States Patent [19]

Lee

[11] Patent Number: 4,723,950
[45] Date of Patent: Feb. 9, 1988

[54] URINE DRAINAGE BAG OUTLET WITH BARRIER AGAINST MICROBIAL INFECTION

[75] Inventor: Clarence C. Lee, Trenton, N.J.

[73] Assignee: C. R. Bard, Inc., Murray Hill, N.J.

[21] Appl. No.: 18,787

[22] Filed: Feb. 20, 1987

Related U.S. Application Data

[63] Continuation of Ser. No. 680,922, Dec. 12, 1984, abandoned.

[51] Int. Cl.$^4$ .............................................. A61M 1/00
[52] U.S. Cl. ................................. 604/322; 604/323; 604/326
[58] Field of Search ............... 604/317, 318, 327, 333, 604/322, 890, 892

[56] References Cited

U.S. PATENT DOCUMENTS

| | | | |
|---|---|---|---|
| 3,566,874 | 3/1971 | Shepherd | 604/265 |
| 3,598,127 | 8/1971 | Wepsic | 604/265 |
| 4,333,480 | 6/1982 | Villari et al. | 604/317 |
| 4,417,892 | 11/1983 | Meisch | 604/349 |
| 4,505,703 | 3/1985 | Gale et al. | 604/317 |
| 4,529,398 | 7/1985 | Wong et al. | 604/327 |

*Primary Examiner*—Stephen C. Pellegrino
*Assistant Examiner*—Gene B. Kartchner
*Attorney, Agent, or Firm*—Kane, Dalsimer, Kane, Sullivan and Kurucz

[57] ABSTRACT

A urine drainage bag having an outlet tube housing a microcidal tube is disclosed. The microcidal tube is manufactured from polymeric materials capable of absorbing and releasing antimicrobial substances in a controllable sustained time release mechanism, activated upon contact with droplets of urine, thereby preventing the retrograde migration of infectious organisms into the drainage bag.

55 Claims, 3 Drawing Figures

URINE DRAINAGE BAG OUTLET WITH BARRIER AGAINST MICROBIAL INFECTION

This application is a continuation of application Ser. No. 680,922, 12/12/84, now abandoned.

BACKGROUND OF THE INVENTION

1. Field of the Invention

The invention relates to closed system urinary drainage bags. More specifically, the invention relates to a device placed in the outlet tube for dispensing an agent for controlling and preventing the retrograde migration of pathogenic microorganisms into the urinary drainage bag.

2. Brief Description of the Prior Art

Urine drainage bags are routinely used by post-operative patients as well as those with urological disorders. Because of injury to the spinal cord, paraplegic patients are unable to control bladder activity and consequently must continuously use a catheter.

In practice, the patient is catheterized and the catheter then connected to the drainage bag through a length of plastic tubing. The bag is normally supported below the level of the patient either from a bed rail or other support and the urine drains by gravity from the patient through the catheter, the tubing and then into a bag via a drip chamber. The bag may be emptied from time to time by means of an outlet tube which is normally closed to prevent leakage. The tube may discharge its contents into any convenient receptacle and then the outlet tube is clamped and the bag reused for the same patient.

The characterized urinary track is one of the most common sites of hospital-acquired infection and in fact accounts for almost thirty percent of such infections. Significant improvements in the prevention of catheter associated infection has been by use of what are known as closed sterile drainage systems. Despite these advances, still over twenty percent of patients with indwelling catheters continue to acquire urinary infections. See Garibaldi et al, New England J. Med., 291: 215-219, 1974. Urine collection bags must be emptied at frequent intervals usually at least once every shift and the removal of bacterially contaminated urine can lead to the spread of urine infection. It is even possible for a patient in the same ward or room shared with a catheterized patient to acquire the infection. In order to minimize cross-contamination, the collected urine must be maintained in sterile condition during the collection period, even when the urine has a high bacterial count when it enters the drainage bag.

Despite the use of the most careful aseptic techniques almost fifty percent of catheterized patients develop an infection when the catheter is in place for twenty-four hours and approximately ninety-eight percent or even more develop an infection of after four days of use of such catheters. This of course is quite harmful to the patient and subjects them to the risk of cystitis and life threatening septicemia. Arch. Internal Med., Vol. 110: 703-711 (1962) and Lancet, Vol. 1,310-312 (1960). The above-noted infections occur due to many circumstances. These include prolonged use of indwelling Foley-type catheters which are often accompanied by absence of sterile insertion and maintenance techniques; having the catheter connected to clean but not sterilized drainage collection containers; and others. The presence of urinary pathogens in the container which multiply and enter the urinary track through the ascending catheter which is a major pathway of infection is quite important. Various attempts have been made to reduce the migration of bacteria through the closed system including the bag, the drip chamber and the tubing connected to the catheter.

The patent to Jinkens et al, U.S. Pat. No. 3,332,442 employs a connector between a catheter and a urine drainage bag for preventing movement of bacteria from the bag to the patient. The three patents of Langston et al, U.S. Pat. Nos. 4,236,517; 4,193,403; and 4,241,733 show a dispensing device which releases paraformaldehyde to control the multiplication of pathogens and prevent migration in catheters. Shaffer U.S. Pat. No. 4,233,263, teaches adding of hydrogen peroxide solution periodically to a urine bag for prevention of bacterial growth. Attempts have been made to provide a one way inlet valve into the urine bag to prevent upward migration. See, for example, U.S. Pat. Nos. 3,312,221 and 4,232,677.

Other attempts have been made to treat the catheter itself with an microbicidal substance. Note U.S. Pat. No. 3,598,127 and the Shepard et al U.S. Pat. Nos. 3,566,874 and 3,695,921 which relate to an antibiotic material in a hydrophilic catheter coating.

U.S. Pat. No. 4,417,892 describes a method of releasing an microbicidal substance by means of a frangible capsule which is inserted into the outlet drainage tube. The capsule must be broken by a nurse or other medical personnel in order to release the active agent.

SUMMARY OF THE INVENTION

It is well known that indwelling catherization of patients, can lead to serious infections. In normal use of the conventional urinary drainage bag, transmission of infection via the outlet drainage tube is of major concern.

In this invention, a microbicidal tube or plug is inserted into a section of the outlet tube. The microbicidal tube is usually made by one of three process. (1) A porous material, such as polypropylene is impregnated with at least one microbicidal agent. It is then coated with a hydrophilic polymer which in response to contact with urine swells, causing the leaching out of the microbicidal substance. (2) A porous material, such as high density polyethylene is impregnated with a hydrophilic polymer and at least one microbicidal agent. (3) The microbicidal tube is made by compounding and co-extruding a polymer, such as silicone, with at least one microbicidal agent, and then coated with a hydrophilic polymer. By appropriate combination of active agents, virtually all pathogens can be effectively eliminated and prevented from entering the urinary bag and further into the catheter.

The present invention is superior in many ways to the methods of prior art. It is a passive dispensing system, thus eliminating the need for human participation, such as is necessary, for example, in the breaking of an antibiotic containing capsule. It is a self-activating system which responds to the presence of body fluids, in this case, urine. The microbicidal substances are released in a timed sequence for an extended period of time, thus creating an effective barrier against migration of infectious organisms into the catheter.

The microcidal tube is easy to prepare using readily available materials and microbicidal substances. The prolonged effectiveness of the invention obviates the need for frequent draining of bags, thus saving on nurse's time. The passive, self-actuating release, likewise is a labor-saving aspect of the present invention. Since the need for human handling is substantially reduced, there is less of a chance for infection due to such contact.

BRIEF DESCRIPTION THE DRAWINGS

DETAILED DESCRIPTION OF THE INVENTION

Figure 1:
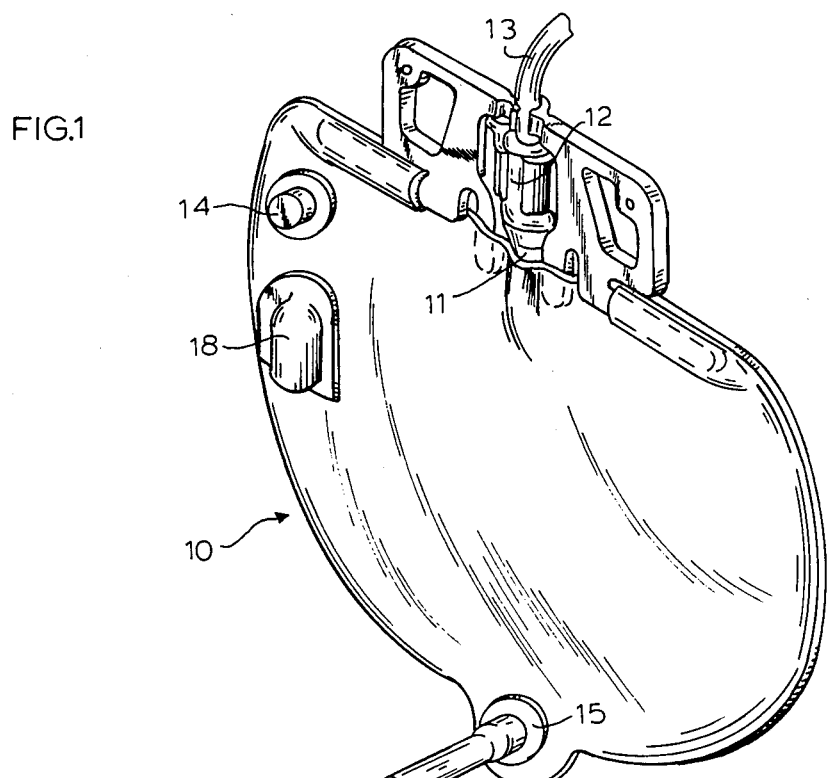
FIG. 1 is a perspective view of a conventional urine drainage bag and showing the outlet tube in broken apart fashion.
Figure 2:
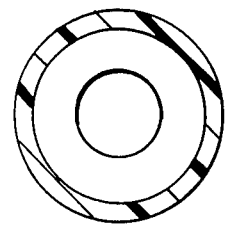
FIG. 2 is an enlarged cross section of the outlet tube taken along the lines 2—2 of FIG. 1.
Figure 3:
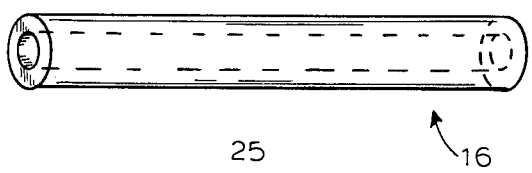
FIG. 3 is a perspective view of a typical microcidal tube used in the outlet tube.

Referring now to the drawings, a conventional closed system urine drainage bag is shown generally at 10 and is formed by peripherally heat sealing or otherwise securing a pair of flat vinyl or PVC sheets. The bag is provided with an inlet 11 adjacent the top thereof for reception of a conventional drip chamber 12 and its associated tubing 13 which connects to a catheter which in turn is inserted in the urethral canal of the patient. An air vent and bacterial filter 14 is conventionally provided on one face of the bag.

The bag also includes a drain 15 terminating in an outlet tube or conduit 16 which may be formed of latex or any other suitable material, and which may be clamped off when not in use in a well known manner by means of the spring pinch clamp or valve 17 which is received about the outlet tube. The free end of the outlet is received in a protective housing 18 heat sealed to one face of the urine drainage bag.

Part of the outlet tube 16 houses a microcidal tube 25. The microcidal tube is typically 1¼ inches in length, 5.5 mm in internal diameter (I.D.), 8.5 mm in outer diameter (O.D.) and is 70% void. It is hollow inside in order to permit unimpeded urine flow. Obviously, the geometry and dimension of the microcidal tube may be varied over wide limits yet still function as a microbial barrier while permitting urine flow.

In general, the microbicidal tube is prepared by impregnating porous polymeric material with at least one microbicidal agent. Various kinds of polymeric materials can be used, but they must be crystalline and have a high melting point which will allow them to withstand exposure to body fluid temperatures without softening. Usually the tube is made by one of three methods. (1) A porous material, such as polypropylene is impregnated with at least one microbicidal agent. It is then coated with a hydrophilic polymer which in response to contact with urine swells, causing the leaching out of the microbicidal substance. (2) A porous material, such as high density polyethylene is impregnated with a hydropholic polymer and at least one microbicidal agent. (3) The microbicidal tube is made by compounding and co-extruding a polymer, such as silicone, with at least one microbicidal agent, and then coated with a hydrophilic polymer.

The solution of the additives and the polymeric material is allowed to react for a suitable length of time in the presence of solvent or solvents. The usual solvents in the preparation of the microcidal tube are ethanol and dimethyl sulfoxide. At the end of the reaction time, the microbicidal tube is dried by conventional methods and sterilized with ethylene oxide (ETO).

The specific antimicrobial substance to be used is left to the choice of the manufacturer, however such substance must readily be compounded into polymers or adhere to the porous polymeric material which in turn will absorb the substance. The biocidal additives can be selected from a very large group of commercially available antibiotics, drugs, antiseptics, etc. Some examples of the common active agents that can be incorporated into the microcidal tube are: penicillin, tetracycline, triclosan, nalidixic acid, sulfamylon, amphotericin B, nonfloxacin, haloprogin, gentamicin, chlorhexidine, clotrimazol, tolnaftate, polymyxin, parachlorometaxylenol, pyrithione, hexachlorophene, nitrofurazone, nitrofurantoin, chlorixin and many others. Microbicidal agents may be incorporated either singly or in various combinations.

The microcidal tube may be inserted inside the outlet tube during normal manufacturing conditions and there will be no loss of the biocidal activity since the substance does not become released until it comes in contact with urine. The microcidal tube is effective for at least two weeks. During this time, it continues to release in a timed sequence, the microbicidal agents, thus creating an effective barrier against upward movement and multiplication of organisms and the subsequent infection of the urinary tract.

The amount of drug released will depend on a number of factors, such as for example, the specific biocidal agent used, the length of time it is desired to release the drug, the dosage that is to be administered in a specific time, etc. The dosage can be controlled by varying the concentrations (or amounts) of the drug(s) and hydrophilic polymer and physical parameters such as pore size and shape of the support polymer used.

There are a number of important advantages that the microbicidal tube offers over the apparatus and methods of prior art.

Thus, the prolonged effectiveness of the microbicidal tube (two weeks at least) saves on nurses' time, for the bag need not be drained as often as it has to be, using prior art apparatus. The passive nature of the sustained drug release, activated upon contact with urine, likewise saves on the nurse's time, for there is no necessity for human participation. Moreover, this is likewise a more reliable and certain method of controlling and preventing infections than methods requiring periodic handling of apparatus. Such periodic manipulation is frequently delayed or entirely disregarded. Additionally, the less human handling that is involved, the less is there a chance for contamination from the outside, hence the decrease in an opportunity for an infection.

The following examples describe the manner and process of making and using the invention and represent the best mode contemplated by the inventor, but are not to be construed as limiting.

The examples and procedures are to be regarded as illustrative rather than restrictive. Variations and changes may be made by those skilled in the art without departing from the spirit of the present investion.

PREPARATION OF MICROCIDAL TUBE

EXAMPLE 1

Batchwise compound 85% polypropylene, 10% hexachlorophene, 4% gentamicin A HCl and 1% clotrimazole at 196° C. and, then, extrude in into a tude. A 1.0 inch segment of the tube is dipped into a solution of 96% ethanol and 4% D-3 polyethylene glycol polyurethane (D-3) for 5 seconds, air-dired at RT for 10 minues and oven dried at 85° C. for 10 minutes.

EXAMPLE 2

Batchwise compound 88% polypropylene, 6% triclosan, 4% chloroxin, and 2% tolnaftate at 198° C. and then extrude it into a tube (5.5 mm ID/8.5 mm OD). A 1.5 inch segment of the tube is dipped into a solution containing 96.5% ethanol and 3.5% D-3 for 5 seconds, air-dried at RT for 10 minutes and oven-dried at 52° C. for 30 minutes.

EXAMPLE 3

Batchwise compound 91% polythylene, 6% nalidixic acid and 3% parachlorometaxylenol at 150° C. to a homogenous dispersion and extrude it into a tude (6.5 mm ID/8.5 mm OD). A 1.0 inch segment of the tube is dipped in a solution containing 97% ethanol and 3% D-3 for 5 seconds, air-dried at RT for 10 minutes and oven-dried at 78° C. for 10 minutes.

EXAMPLE 4

Batchwide compound 89.8% polyethylene, 8% zinc pyrithione and 2.2% tetracycline HCl at 152° C. to a homogenous dispersion and extrude it into a tube (6.5 mm ID/8.5 mm OD). A 1.5 inch segment of it is dipped in a solution of 95% ethanol and 5% D-3 for 5 seconds, air-dried at RT for 10 minutes and oven-dried at 65° C. for 10 minutes.

EXAMPLE 5

A segment of microporous polysulfone tube is immersed in a solution of 88.8% ethanol, 7% gentamicin A HCl, 4% D-3 polyethylene glycol polyurethane and 0.2% zinc pyrithione for 10 minutes. It is then air-dried at room temperature (RT) for 10 minutes and oven-dried at 70° C. for 15 minutes. The concentration of gentamicin A HCl is below its saturation point and could be raised if wanted. Zinc pyrithione, an antifugal agent, is approximately at its optimum concentration. It could be replaced bythe more soluble sodium pyrithione.

EXAMPLE 6

A segment of microporous polysufone tube is immersed in a solution of 79.5% ethanol, 11% tetracycline HCl, 5.3% polymyxin B HCl, 3.5% D-3 polyethylene glycol polyurethane and 0.2% zinc pyrithione for 10 minutes. It is air-dried at RT for 10 minutes and oven-dried at 68° C. for 20 minutes. Both tetracycline and polymyxin are below their saturation points.

EXAMPLE 7

A segment of microporous high density polyethylene tube (HDPE; pore size: 50 microns) is immersed in a solution of 50% anhydrous acetone, 40% anyhydrous ethanol, 5% gentamicine HCl, and 5% parachlorometaxylenol for 5 minutes. It is air-dried at RT for 15 minutes, dipped in 96.5% ethanol, 3.5% D-3 polyethylene glycol polyurethane for 5 seconds, air-dired at RT for 10 minutes and oven-dried at 70° C. for 15 minutes. Concentrations of D-3, gentamicine and parachlorometaxylenol could be increased if needed.

EXAMPLE 8

A segment of microporous HDPE is immersed in a solution of 73% ethanol, 10% tetracycline HCl, 10% parachlorometaxylenol, 3.8% D-3, 2% dimethyl sufoxide (DMSO), 0.6% clotrimazol and 0.6% tolnaftate for 5 minutes. It is then air-dried at RT for 10 minutes, oven-dried at 55° C. for 20 minutes, and air-dried at RT for 18 hours.

EXAMPLE 9

A segment of HDPE tube is immersed in a solution of 41.4% DMSO, 44.6% acetone, 10% triclosano and 4.3% chloroxine for 10 minutes. It is air-dried at RT for 15 minutes, dipped into 96.5% ethanol and 3.5% D-3 for 5 seconds, air-dried at RT for 10 minutes and oven-dried at 55° C. for 30 minutes. Concentrations of triclosan and chloroxine could be raised substantially if needed.

EXAMPLE 10

A segment of microporous polypropylene tube (5.5 mm ID/8.5 mm OD; 70% void) is immersed in a solution of 83.5% anhydrous acetone, 8% chlorhexidine acetate, 5.5% triclosan and 3% Hypol 3000 polyurethane for 5 minutes. It is air-dried at RT for 5 minutes, oven-dried at 52° C. for 10 minutes and air-dried at RT for 18 hours. Concentrations of chlorhexidine and triclosan can be increased if needed.

EXAMPLE 11

A segment of microporous polypropylene tube is immersed in a solution containing 50% ehtanol, 33% chloroform, 11% hexachlorophene, 3.8% D-3, 1% nalidixic acid, 0.6% clotrimazole and 0.6% tolnaftate for 10 minutes. It is air-dried at RT for 10 minutes and oven-dried at 72° C. for 25 minutes. Concentrations of clotrimazole and tolnaftate are substantially below their saturation points in the solvent system.

EXAMPLE 12

A segment of microporous polypropylene tube is immersed in a solution of 46.2% ethanol, 22% DMSO, 11% parachlorometa xylenol, 11% dchlorhexidine diacetate, 4.8% water, 4.0% D-3 and 1.0% nitrofarazone for 10 minutes. It is air-dried at RT for 10 minutes, oven-dried at 68° C. for 10 minutes and air-dried at RT for 18 hours. The concentration of parachlorometaxylenol could be increased if needed.

EXAMPLE 13

A segment of microporous polypropylene tube is immersed in a solution containing 84% ethanol, 7.5% hexachlorophane, 5% D-3, 2.5% DMSO, 0.7% $H_2O$, 0.25% clotrimazole and 0.05% aminacrine for 10 minutes. It is air-dried at RT for 10 minutes, oven-dried at 78° C. for 20 minutes and air-dried at RT for 18 hours.

EXAMPLE 14

A segment of microporous polypropylene tube is immersed in a solution of 50.5% ethanol, 31% acetone, 10% hexachlorophene, 4.3% D-3, 2.5% DMSO, 1% clotrimazole an d0.5% $H_2O$ for 10 minutes. It is air-dried at RT for 10 minutes, oven-dried at 78° C. for 20 minues, and air-dried at RT for 18 hours.

EXAMPLE 15

A segment of microporous polypropylene tube is immersed in a solution containing 44.1% ehtanol, 31% DMSO, 11% triclosan, 9% hexachlorophene, 3.4% D-3, 1.0% clotrimazole, and 0.5% nitrofuragon for 10 minutes. It is air-dried at RT for 15 minutes, oven-dried at 52° C. for 30 minutes and air-dried at RT for 18 hours.

Concentrations of triclosan, hexachlorophene and clotrimazole could be increased if needed.

The foregoing preparations of microbicidal tubes were effective in maintaining sterility for 17 to 21 days upon exposure to urine.

What is claimed is:

1. An outlet for a urine drainage bag, comprising:
   an outlet tube secured to the bottom part of the urine drainage bag; and
   an independently formed microbicidal tube housed in and connected to the interior of the outlet tube, comprising means for storing and means for releasing one or more microbicidal substances, said means for storing the microbicidal substance/s being a porous material, said means of releasing the microbicidal substance/s being a hydrophilic polymer which in response to contact with urine swells causing the leaching out of the microbicidal substance, said microbicidal substance capable of being passively and controllably released in a long term sustained time sequence without human intervention to create an effective barrier against movement and multiplication or organisms and subsequent infection of the urinary tract.

2. The outlet according to claim 1 wherein the means of storing the microbicidal substance/s is a porous polypropylene material.

3. The outlet according to claim 1 wherein the hydrophylic polymer is D-3 polyethylene glycol polyurethane.

4. The outlet according to claim 1 wherein the microbicidal substances are hexachlorophene, gentamycin and clotrimazol.

5. The outlet according to claim 1 wherein the microbicidal substances are triclosan, chloroxin and tolnaftate.

6. The outlet according to claim 1 wherein the microbicidal substances are nalidixic acid and parachlorometaxylenol.

7. The outlet according to claim 1 wherein the microbicidal substances are zinc pyrithione and tetracycline.

8. The outlet according to claim 1 wherein the microbicidal substances are gentamycin and zinc pyrithione.

9. The outlet according to claim 1 wherein the microbicidal substances are tetracycline polymyxin and zinc pyrithione.

10. The outlet according to claim 1 wherein the microbicidal substances are gentamycin and parachlorometaxylenol.

11. The outlet according to claim 1 wherein the microbicidal substances are tetracycline, parachlorometaxylenol, clotrimazol and tolnaftate.

12. The outlet according to claim 1 wherein the microbicidal substances are triclosan and chloroxin.

13. The outlet according to claim 1 wherein the microbicidal substances are chlordexidine and triclosan.

14. The outlet according to claim 1 wherein the microbicidal substances are chloroform, hexachlorophene, nalidixic acid, clotrimazol and tolnaftate.

15. The outlet according to claim 1 wherein the microbicidal substances are parachlorometaxylenol, chlorhexidine and nitrofurazone.

16. The outlet according to claim 1 wherein the microbicidal substances are hexachlorophane, clotrimazol and aminacrine.

17. The outlet according to claim 1 wherein the microbicidal substances are hexachlorophene, and clotrimazol.

18. The outlet according to claim 1 wherein the microbicidal substances are triclosan, hexachlorophene, clotrimazole and nitrofurazano.

19. A method of treating the outlet tube of a urinary drainage bag to prevent passage and/or growth of microorganisms comprising:
    the insertion of a microbicidal tube inside the outlet tube, said microbicidal tube being porous with a hydrophilic polymer disposed throughout and containing at least one microbicidal substance, whose release is passively activated during drainage of urine, the hydrophilic polymer in response to contact with urine swells causing leaching out of the microbicidal substance, whereby it acts upon the present microorganisms without human intervention to create an effective barrier against movement and multiplication of organisms and subsequent infection of the urinary tract.

20. A urinary drainage system comprising a sustained time release barrier incorporated therein, said barrier comprising means for storing and means for passively and controllably releasing at least one microbicidal substance, said means for storing the microbicidal substance/s being a porous material, said means of releasing the microbicidal substance/s being a hydrophilic polymer which in response to contact with urine swells causing the leaching out of the microbicidal substance, said microbicidal substance capable of being passively and controllably released in a long term sustained time sequence without human intervention to create an effective barrier against movement and multiplication of organisms and subsequently infection of the urinary tract.

21. The urinary drainage system according to claim 20 wherein the means of storing the microbicidal substance/s is a porous polypropylene material.

22. The urinary drainage system according to claim 20 wherein the hydrophilic polymer is D-3 polyethylene glycol polyurethane.

23. The urinary drainage system according to claim 20 wherein the microbicidal substances are hexachlorophene, gentamycin and clotrimazole.

24. The urinary drainage system according to claim 20 wherein the microbicidal substances are triclosan, chloroxin and tolnaftate.

25. The urinary drainage system according to claim 20 wherein the microbicidal substances are nalidixic acid and parachlorometaxylenol.

26. The urinary drainage system according to claim 20 wherein the microbicidal substances are zinc pyrithione and tetracycline.

27. The urinary drainage system according to claim 20 wherein the microbicidal substances are gentamycin and zinc pyrithione.

28. The urinary drainage system according to claim 20 wherein the microbicidal substances are tetracycline polymyxin and zinc pyrithione.

29. The urinary drainage system according to claim 20 wherein the microbicidal substances are gentamycin and parachlorometaxylenol.

30. The urinary drainage system according to claim 20 wherein the microbicidal substances are tetracycline, parachlorometaxylenol, clotrimazol and tolnaftate.

31. The urinary drainage system according to claim 20 wherein the microbicidal substances are triclosano and chloroxin.

32. The urinary drainage system according to claim 20 wherein the microbicidal substances are chlordexidine and triclosan.

33. The urinary drainage system according to claim 20 wherein the microbicidal substances are chloroform, hexachlorophene, nalidixic acid, clotrimazol and tolnaftate.

34. The urinary drainage system according to claim 20 wherein the microbicidal substances are parachlorometaxylenol, chlorhexidine and nitrofurazone.

35. The urinary drainage system according to claim 20 wherein the microbicidal substances are hexachlorophane, clotrimazol and aminacrine.

36. The urinary drainage system according to claim 20 wherein the microbicidal substances are hexachlorophene, and clotrimazol.

37. The urinary drainage system according to claim 20 wherein the microbicidal substances are triclosan, hexachlorophene, clotrimazole and nitrofurazano.

38. A microbicidal tube, comprising means for storing and means for releasing one or more antimicrobial substance/s capable of being passively and controllably released in a sustained time sequence, said means for storing the microbicidal substance/s being a porous material, said means of releasing the microbicidal substance/s being a hydrophilic polymer which in response to contact with urine swells causing the leaching out of the microbicidal substance said microbicidal substance capable of being passively and controllably released in a long term sustained time sequence without human intervention to create an effective barrier against movement and multiplication of organisms and subsequently infection of the urinary tract.

39. The microcidal tube according to claim 38, wherein the means of storing the microbicidal substance/s is a porous polypropylene material.

40. The microbicidal tube according to claim 38 wherein the hydrophilic polymer is D-3 polyethylene glycol polyurethane.

41. The microbicidal tube according to claim 38 wherein the microbicidal substances are hexachlorophene, gentamycin and clotrimazol.

42. The microbicidal tube according to claim 38 wherein the microbicidal substances are triclosan, chloroxin and tolnaftate.

43. The microbicidal tube according to claim 38 wherein the microbicidal substances are nalidixic acid and parachlorometaxylenol.

44. The microbicidal tube according to claim 38 wherein the microbicidal substances are zinc pyrithione and tetracycline.

45. The microbicidal tube according to claim 38 wherein the microbicidal substances are gentamycin and zinc pyrithione.

46. The microbicidal tube according to claim 38 wherein the microbicidal substances are tetracycline polymyxin and zinc pyrithione.

47. The microbicidal tube according to claim 38 wherein the microbicidal substances are gentamycin and parachlorometaxylenol.

48. The microbicidal tube according to claim 38 wherein the microbicidal substances are tetracycline, parachlorometaxylenol, clotrimazol and tolnaftate.

49. The microbicidal tube according to claim 38 wherein the microbicidal substances are triclosano and chloroxin.

50. The microbicidal tube according to claim 38 wherein the microbicidal substances are chlordexidine and triclosan.

51. The microbicidal tube according to claim 38 wherein the microbicidal substances are hexachlorophene, nalidixic acid, clotrimazol and tolnaftate.

52. The microbicidal tube according to claim 38 wherein the microbicidal substances are parachlorometaxylenol, chlorhexidine and nitrofurazone.

53. The microbicidal tube according to claim 38 wherein the microbicidal substances are hexachlorophane, clotrimazol and aminacrine.

54. The microbicidal tube according to claim 38 wherein the microbicidal substances are hexachlorophene, and clotrimazol.

55. The microbicidal tube according to claim 38 wherein the microbicidal substances are triclosan, hexachlorophene, clotrimazole and nitrofurazano.

* * * * *